United States Patent [19]

Conway et al.

[11] 4,097,261

[45] Jun. 27, 1978

[54] METHOD AND COMPOSITIONS FOR CONTROLLING WATERHYACINTH

[75] Inventors: Kenneth Edward Conway; Thomas Edward Freeman; Raghavan Charudattan, all of Gainesville, Fla.

[73] Assignee: Abbott Laboratories, North Chicago, Ill.

[21] Appl. No.: 796,565

[22] Filed: May 13, 1977

[51] Int. Cl.[2] .......... A01N 9/00

[52] U.S. Cl. .......... 71/66

[58] Field of Search .......... 71/66

[56] References Cited

PUBLICATIONS

Water Resources Research Center Publication No. 30, University of Florida, (Gainesville).

Conway, Can. J. Bot., vol. 54: 1079–1083.

*Primary Examiner*—Catherine L Mills

*Attorney, Agent, or Firm*—Gildo E. Fato; Robert L. Niblack

[57] ABSTRACT

Disclosed are compositions for and a method for controlling waterhyacinth. The compositions and method utilize the fungus *Cercospora rodmanii* Conway.

10 Claims, No Drawings

METHOD AND COMPOSITIONS FOR CONTROLLING WATERHYACINTH

BACKGROUND OF THE INVENTION

As an alternative to chemical pest control, the use of naturally occurring biological agents provide many advantages. The use of biologicals should reduce the environmental impact of chemicals as well as providing safety advantages to non-target life forms.

The use of native plant pathogens for biological control of weeds can be considered as a specific alternative to chemical herbicides. The native pathogen in the natural state exists along with its host and of necessity must not be totally destructive in the native habitat or the pathogen too would disappear. However, it should be possible to use a pathogen which normally is native in such a way as to overcome the host defenses and produce sufficient disease in the host to affect biological control. This invention describes the conditions under which waterhyacinth can be controlled by a native pathogen. The noxious waterhyacinth (*Eichornia crassipes* (Mart.) Solms) was first introduced into the state of Florida in the 1890's. Since then, it has spread and now covers nearly 300,000 acres of waterways. The Florida Department of Natural Resources estimates that 10–15 million dollars are spent annually in Florida for aquatic weed control with a majority being spent on waterhyacinth control.

Control of waterhyacinths has been attempted by three techniques; mechanical removal, chemical control and biological control. Waterhyacinth is a good candidate for biological control because its main means of reproduction and spread is asexual through offshoots. Insects have been the organisms used most in biological control of waterhyacinth. In 1970, a biological control program for aquatic weeds using plant pathogens was initiated at the University of Florida. As part of this program, foreign and domestic surveys were made on waterhyacinth and other target aquatic weeds.

Particular interest has centered on a naturally occurring decline of waterhyacinth in the Rodman Reservoir, a large area of impounded water in the Cross-Florida Barge Canal. This decline was first evident in the spring of 1971; large populations of waterhyacinth in the reservoir were effected. Symptoms of the disease included chlorosis of the plants, failure to produce offshoots, spindly petioles, and a root rot. These symptoms increased in severity over the growing season. It was assumed at that time that the root rot was the primary cause of the decline. Each year since 1971 the decline lessened in intensity until 1974 when very few affected plants were noted. A comprehensive survey was begun in 1973 of fungi occurring on waterhyacinth in the Rodman Reservior (Conway, K. E., T. E. Freeman, and R. Charvdattan, The Fungal Flora of Waterhyacinth in Florida, Part 1. Water Resources Research Center Publication No. 30, University of Florida, Gainesville). Among the fungi isolated was a *Cercospora sp.* that later was named *C. rodmanii* Conway (Conway, K. E., Can. J. Bot. 54:1079–1083).

The initial objective of this study was to demonstrate the usefulness of *C. rodmanii* in infecting waterhyacinths under field conditions. This objective was expanded during the second year to continue the infection on the plants throughout the year and to determine the optimal time for application of the fungal inoculum.

DETAILED DESCRIPTION OF THE INVENTION

The fungal isolate obtained as described above was evaluated through a three-stage testing program to demonstrate its usefulness:

The first stage comprised primary greenhouse testing — *Cercospora rodmanii* (isolate WH-9) was grown on potato-dextrose agar with 0.5% yeast extract added (PDAY). Individual waterhyacinths were placed in plastic-lined pots that contained one liter of water with 5 ml of a solution of 0.2 M Fe(NH) SO.H O and 0.2 M MgSO.7H O added.

Several areas on the waterhyacinth leaves and petioles were gently rubbed to break the cuticle. Mycelia and conidia were scraped from the agar surface and placed on these spots. A plastic bag was placed over the entire plant for 2 weeks. After 3 weeks, the inoculated leaves of waterhyacinths became chlorotic and necrotic spots were present on both the leaves and petioles of the plants where the inoculum had been placed. The spots on the leaves extended to the leaf tip.

In the second stage greenhouse testing, 25 to 30 waterhyacinths were grown in a large vat of water. The fungus was cultured in five Roux bottles containing 100 ml of potato-dextrose broth with 0.5% yeast extract added. After 12 days, the mycelial mats were collected and comminuted in a Waring blender for 15 seconds. The resulting suspension was sprinkled onto non-wounded waterhyacinths, which more closely approached inoculation as it occurs under natural conditions. The plants were not covered following inoculation. Within 1 month after inoculation, the plants in the vat showed chlorosis, and many showed necrotic spots. The plants were in an obvious state of decline. Spots extending to the leaf tip similar to those of the primary test were not noted. After several months, the plants became severely stunted, developed symptoms of root rot, and eventually died.

The third stage comprised field testing. An isolated pool (1.7 ha) of Lake Alice, Gainesville Florida, was chosen as a suitable site for the first field test to demonstrate utility of *C. rodmanii* in the control of waterhyacinth. The fungus was grown in 100 Roux bottles containing 100 ml PDY broth. The macerated mycelia and conidia were diluted with 38 liters of water and sprayed on waterhyacinths. The fungus was applied to waterhyacinths in the evening to utilize the cooler night temperatures and high relative humidity, thus promoting infection. The area sprayed represented an arc of 6.4 meter radius from the shoreline for a coverage of 64.6 m. Approximately 1 kilogram (kg) (wet weight) of the fungus was used per application. Two applications of the fungus were applied to waterhyacinths, one on 4 September and the second on 3 October 1974.

The presence of *C. rodmanii* was confirmed by reisolation from the diseased plants in the inoculated area. By Nov. 1, 1974, tip dieback and other symptoms were evident throughout the entire pool area. *Cercospora rodmanii* was isolated from the diseased plants on the opposite side of the pool from the inoculated area to confirm and demonstrate the organism spread from the initial source of infection. An aerial view of the Lake on Nov. 21, 1974 showed a gradient of infection extending from the inoculated area through the pool area and into the main lake. Frost was first officially recorded in December and the diseased plants in the pool area were killed to the water surface. However, plants in the middle of the main lake continued to stay green. In February 1975, regrowth of waterhyacinths was delayed longer in the pool area than in the main lake. The waterhyacinths in the pool were reinoculated in the spring of 1975 and disease symptoms and severity have been monitored since then with no additional inoculations.

Results of the described test establish that *C. rodmanii* can infect waterhyacinth, and that once established it can spread from a source of infection, to result in effective management of waterhyacinth.

The following examples serve to further describe and typify the invention.

EXAMPLE 1

A second field test to that previously described was conducted in Lake Concordia, La. (June–November 1975) and comprised a large scale test to demonstrate the effect of an integrated control of plant pathogens and insects on waterhyacinths. Plants were grown in 2m × 2m floating frames with screen bottoms. Two pathogenic fungi were used, *C. rodmanii* and *Acremonium zonatum* (Sawada) Gams, applied at the rates of 48 gm/m and 96 gm/m, respectively. These fungi were tested alone and in combination with two insects *Arzama densa* Walker (40 insects/frame) and *Neochetina eichhorniae* Warner (50 insects/frame). The test was monitored every two weeks and data on the weight of the plants in the frames, height of plants and number of flowers were recorded. A significant reduction in the weight of waterhyacinths in the frames occurred when pathogens and insects were used in combinations of three and four (per frame).

EXAMPLE 2

A third test was conducted in small containers (0.4m, surface area). The purpose was to determine the effect of increasing inoculum rates of *C. rodmanii* (24 gm/m, 48 gm/m, 96 gm/m) on disease incidence and damage to waterhyacinths. Ten plants with all dead leaves removed were placed in each container and the number of living leaves per container was recorded. The containers and treatments were arranged in a Latin square design. The fungus was applied by shaking cominuted mycelia and conidia onto the plants. Data were recorded every 2 weeks and included the number of plants, number of flower stalks, number of living leaves, number of dead leaves, and the length of the longest leaf and root per container.

Results showed that an inoculum was effective at a rate of 96 gm/m which significantly increased the number of dead leaves per plant.

EXAMPLE 3

A fourth test was conducted in Rodman Reservoir where the disease had been originally isolated. An area of waterhyacinth was chosen which was inaccessible to most boats so that the intrusion by man was minimal. Five inoculations, one each at two week intervals, were applied to waterhyacinths from the shoreline starting in February 1975. A sixth application was placed on waterhyacinth in a cypress tree area. Repeated inoculations were considered necessary to initiate infection and create an epiphytotic situation. By mid-April, damage to the plants due to *C. rodmanii* was evident in the inoculated areas. There was a definite reduction of plant growth and size in test plots when compared to uninoculated waterhyacinth that surrounded these areas. In July, waterhyacinths in the inoculated areas demonstrated typical *C. rodmanii* symptoms and plants were beginning to decline, die and sink below the surface of the water. An aerial view in August 1975 of the area showed continued infection and sinking of waterhyacinths with approximately 10–20 acres of open water where there had been none at the beginning of the test. Large mats of waterhyacinths showed the typical *C. rodmanii* symptoms; small punctate spotting on the leaves and petioles, necrosis of the leaf tips and root rot. By mid-October, the area of open water was estimated to be 30–40 acres. A reestablishment of open areas with 10–15 acres of waterhyacinth occurred over the winter. However, these plants were infected with *C. rodmanii* and have acted as a source of inoculum during the Spring of 1976. During June 1976, above average rainfall necessitated a change in the water flow patterns into the Reservoir which increased the inflow of more nutritious water from the eutrophic head lakes. This increased nutrition resulted in a more rapid elongation of the newly formed leaves of waterhyacinths which limited the disease to the lower canopy of the plants. However, the lower leaves were still heavily infected with *C. rodmanii* and during the early part of August foci of disease were noted in the waterhyacinth area.

Several significant facts concerning the efficacy of *C. rodmanii* resulted from the field test at Rodman Reservoir. It was shown that *C. rodmanii* was effective by spreading from an area of infection and caused large areas of waterhyacinths to die and sink below the surface of the water. The organism was also capable of overwintering on the older leaves of waterhyacinth and provided an inoculum source to establish the disease during the next growing season. A complete elimination of the diseased plants would have prevented the continuation of the disease in the spring which is a consideration that must be recognized in future aquatic plant management designs. The ability of *C. rodmanii* to control the growth of waterhyacinth depends on its ability to infect newly formed leaves. When all factors are optimal for infection the plant appears to put most of its energy into leaf production and as the pathogen kills the leaves the plant becomes depleted, declines and dies. The root area then becomes more susceptible to invasion by rot producing microorganisms. The increased growth of waterhyacinths that occurred during the summer of 1976 also emphasizes the importance of an overall systems management approach that will favor conditions conducive to biological control agents.

*C. rodmanii* is a pathogen of only waterhyacinth, as demonstrated by a host specificity determinations conducted on over 80 varieties of economically and ecologically important plants of Florida. A modified centrifugal (related plants) and varietal (economic plants) testing strategy was utilized to determine plants to be tested. Host specificity testing was also conducted on economically important plants of Louisiana prior to field evaluations showed that the host range of *C. rodmanii* was limited to waterhyacinths and therefore could be employed in field tests with a considerable degree of safety. The results of this study are shown in Table I.

TABLE I

Plants included in Greenhouse and Field Host Specificity Testing of *Cercospora rodmanii.*

| Host | Rating: Greenhouse | Rating: Field |
|---|---|---|
| Amaranthaceae | | |
| *Alternanthera philoxeroides* | | |

TABLE I-continued

Plants included in Greenhouse and Field Host Specificity Testing of *Cercospora rodmanii*.

| Host | Rating Greenhouse | Field |
|---|---|---|
| (Mart.) Griseb. | | |
| Alligatorweed | —— | —— |
| Araceae | | |
| *Xanthosoma sagittaefolium* | | |
| (L.) Schott | | |
| Elephants-Ear | —— | —— |
| Chenopodiaceae | | |
| *Beta vulgaris* L. | | |
| Beet "Detroit Dark Red" | —— | —— |
| "Early Wonder" | —— | —— |
| *Spinacia oleracea* L. Spinach | — | — |
| Commelinaceae | | |
| *Zebrina pendula* Schnizl. | | |
| Wandering Jew | —— | NT |
| Compositae | | |
| *Cichorium endivia* L. | | |
| Endive | | |
| "Full Heart Batavia Escarole" | —— | NT |
| "Green Curled" | —— | NT |
| *Lactuca sativa* L. | | |
| Lettuce "Great Lakes" | —— | +— |
| "Bibb" | —— | +— |
| Convolvulaceae | | |
| *Ipomoea batatas* (L.) Lam. | | |
| Sweet Potato "Georgia Red" | —— | —— |
| Cruciferaceae | | |
| *Brassica oleracea* var. *capitata* L. | | |
| Cabbage "Charleston Wakefield" | —— | —— |
| *B. oleracea* var. *acephala* L. | | |
| Collards "Georgia" | —— | —— |
| *B. juncea* (L.) Coss | | |
| Mustard "Florida Broad Leaf" | —— | —— |
| *Raphanus sativus* L. | | |
| Radish "Scarlet Red Globe" | —— | —— |
| Cucurbitaceae | | |
| *Citrullus vulgaris* Schrad. | | |
| Watermelon "Charleston Grey" | —— | —— |
| "Congo" | —— | NT |
| "Crimson Sweet" | —— | —— |
| *Cucumis sativus* L. | | |
| Cucumber "Pickling F-1 Hybrid" | —— | —— |
| "Poinsett" | +— | —— |
| *C. melo* L. var. *reticulatus* | | |
| Naud. Canteloupe | | |
| "Hale Best Jumbo" | —— | —— |
| *Cucurbita pepo.* L. var. *melopepo* | | |
| Squash | | |
| "Early Summer Crook Neck" | +— | —— |
| Gramineae | | |
| *Avena Sativa* L. | | |
| Oats "Fulghum" | —— | —— |
| *Cynodon dactylon* (L) pers. | | |
| Bermudagrass | —— | NT |
| *Lolium multiflorum* Lam. | | |
| Ryegrass | —— | NT |
| *Oryza sativa* L. | | |
| Rice "Saturn" | —— | —— |
| *Saccharum officinarum* L. | | |
| Sugarcane | —— | —— |
| *Secale cereale* L. | | |
| Rye "Weser 1973" | —— | —— |
| *Stenotaphrum secundatum* (Walt.) Kunze | | |
| St. Augustinegrass | —— | NT |
| *Triticum vulgare* Vill. | | |
| Wheat "Hadden" | —— | —— |
| *Zea mays* L. | | |
| Corn "Florida Sweet" | —— | —— |
| "Funks 4762" | —— | —— |
| "Funks 5945" | —— | —— |
| "Golden Hybrid NK 199" | —— | —— |
| Pag 751" | —— | —— |
| "Silver Queen" | —— | —— |
| Hydrocharitaceae | | |
| *Hydrilla verticillata* Royle | | |
| Hydrilla | —— | —— |
| *Limnobium spongia* (Bosc.) Steud. | | |
| Frogbit | —— | —— |
| Lauraceae | | |
| *Persea americana* Mill. | | |
| Avocado | —— | —— |
| Leguminosae | | |
| *Arachis hypogaea* L. | | |
| Peanut "Florunner" | —— | —— |
| *Glycine max* (L.) Merr. | | |
| Soybean "Bragg" | —— | —— |
| "Davis" | —— | NT |
| *Phaseolus limensis* Macf. | | |
| Lima "Fordhook" | —— | —— |
| "Henderson Bush" | —— | —— |

TABLE I-continued

Plants included in Greenhouse and Field Host Specificity Testing of *Cercospora rodmanii*.

| Host | Rating Greenhouse | Field |
|---|---|---|
| "Jackson Wonder | | |
| Speckled Butter" | —— | —— |
| *Phaseolus vulgaris* L. | | |
| Bush Bean "Bountiful" | NT | —— |
| Harvest Bean | —— | —— |
| Runner "Kentucky Wonder" | —— | —— |
| *Vigna sinensis* L. | | |
| "White Acre Pea" | —— | —— |
| "Cowpea Zipper Cream" | —— | —— |
| Liliaceae | | |
| *Allium cepa* L. | | |
| Onions "Purple" | —— | —— |
| "White" | —— | —— |
| "Yellow" | —— | —— |
| Malvaceae | | |
| *Gossypium hirustum* L. | | |
| Cotton "DPL 16" | —— | NT |
| "Sea Island" | —— | —— |
| "Stoneville 213" | —— | NT |
| *Hibiscus esculentus* L. | | |
| Okra "Clemson Spineless" | —— | —— |
| Nymphaeaceae | | |
| *Nuphar luteum* (L.) | | |
| Sibthorp and Smith Cow Lily | —— | —— |
| Pinaceae | | |
| *Pinus elliotii* Engelm. | | |
| Slash Pine | —— | —— |
| Pontederiaceae | | |
| *Eichhornia crassipes* (Mart.) Solms | | |
| Waterhyacinth | ++ | ++ |
| *Pontederia cordata* L. | | |
| Pickerelweed | —— | —— |
| Rhizophoraceae | | |
| *Rhizophora mangle* L. | | |
| Red Mangrove | —— | NT |
| Rosaceae | | |
| *Fragaria chiloensis* Duchesne | | |
| Strawberry "Florida 90" | —— | —— |
| *Pyracantha coccinea* Roem. | | |
| Firethorn | —— | —— |
| Rutaceae | | |
| *Citrus paradisi* Macf. | | |
| Grapefruit "Duncan" | —— | —— |
| *C. limon* (L.) Burm. | | |
| Lemon | —— | —— |
| *C. aurantium* L. | | |
| Orange "Sour" | —— | —— |
| *C. sinesis* (L.) Osbeck | | |
| Orange "Sweet" | —— | —— |
| *C. reticulata* Blanco | | |
| Tangerien | — | — |
| Solanaceae | | |
| *Capsicum frutescens* L. | | |
| Sweet Pepper | | |
| "Early Cal Wonder P-25" | —— | —— |
| *Capsicum* sp. | | |
| Banana Pepper | —— | —— |
| Banana Pepper | —— | —— |
| "Hot Hungarian" | NT | —— |
| *Lycopersicon esculentum* Mill. | | |
| Tomatoes | | |
| "Homestead" | —— | —— |
| "Manalucie" | —— | —— |
| "MH-1" | —— | —— |
| "Walter" | NT | —— |
| *Nicotiana tabacum* L. | | |
| Tobacco "Turkish NN" | —— | —— |
| *Solanum melogena* L. | | |
| Eggplant "Florida Strain M" | —— | —— |
| *S. tuberosum* L. | | |
| Potato "Sebago" | | |
| "Red LaSoda NT" | —— | —— |
| Umbelliferae | | |
| *Apium graveolens* L. var. *dulce* DC. | | |
| Celery "Giant Pascal" | +— | NT |
| "Utah 52-14" | —— | NT |
| *Daucus carota* L. var. *sativa* DC | | |
| Carrot "Imperator" | —— | —— |
| *Hydrocotyle ranunculoides* L. | —— | —— |
| *H. umbellata* L. | —— | —— |

Key
—— Not susceptible
+— Infection only on older and/or dying leaves
++ Infection on living leaves
NT Not tested This mycoherbicide may be utilized effectively in deverse formulations, including the agronomically acceptable adjuvants and carriers normally employed for facilitating the dispersion of active ingredients for agricultural applications, recognizing a known fact that the dosage, formulation, mode of application of a chemical agent and other variables may affect its activity in any given application. Thus, the previously described mycoherbidide may be formulated as a suspension or dispersion, in aqueous or non-aqueous media, as a dust, as a wettable powder, as an emulsifiable concentrate, as a granule, or as any of several other known types of formulations, depending on the desired mode of application. These herbicide compositions may be applied as sprays, dust, or granules to the plant situs against which herbicidal activity is desired.

In order to provide compositions in the form of dust, granules, water dispersible powders, aqueous dispersions, or emulsions and dispersions in organic liquids, the carrier or diluent agent in such formulations may be a finely divided solid, an organic liquid, water, a wetting agent, a dispersing agent, or emulsifying agent, or any suitable combination of these. Generally, when liquids and wettable powders are prepared a conditioning agent comprising one or more surface-active agents or surfactants is present in amounts sufficient to render a given composition containing the active material, the microorganism, dispersible in water or in oil. The microorganism, the fungi *Cercospora rodmanii* Conway, is obtained by conventional submerged culture fermentation. To convert it to a form which will facilitate the preparation of the following described compositions, a slurry is prepared which is then dried onto a primary, agronomically acceptable carrier such as vermiculite, whereby the microorganism is adsorbed onto the carrier. The microorganism, adsorbed onto the carrier, becomes the concentrate for preparing the desired composition. If desired, the slurry can be used as the concentrate for herbicidal compositions.

The surface active agent used in the invention can be a wetting dispersing or emulsifying agent which will assist dispersion of the effective composition. The surface-active agent or surfactant can include such anionic, cationic and non-ionic agents as have heretofore been generally employed in plant control compositions of similar type. Suitable surface-active agents are set forth, for example, in "Detergents and Emulsifiers" 1971 Annual by John W. McCutcheon, Inc.

In general, 1–10% by weight of the surface-active agent will be used in compositions of this invention and ordinarily the amount of surface-active will range from 1–5% but may even be less than 1% by weight.

Additional surface-active agents can be added to formulations to increase the ratio of surfactants: active ingredients up to as high as 5:1 by weight. Such compositions may have a greater biological effectiveness than can be expected when the components are used separately. When used at higher ratios, it is preferred that the surfactant be present in the range of one-fifth to five parts surfactant for each one part of active agent.

The following are more detailed formulations exemplifying the various compositions.

EXAMPLE 4

Wettable Powders

Wettable powders are water-dispersible compositions containing the active material, an inert solid extender, and one or more surfactants to provide rapid wetting and to prevent heavy flocculations when suspended in water.

The inert extenders which are preferred for use in the wettable powders of this invention containing the active compounds are of mineral origin.

Extenders suitable for the wettable powder formulations of this invention are the natural clays, diatomaceous earth and synthetic mineral fillers derived from silica and silicate. Most preferred fillers for this invention are kaolinites, attapulgite clay, montmorillonite clays, synthetic silicas, synthetic magnesium silicate and calcium sulfate dihydrate.

Among the more preferred surfactants are the nonionic and anionic types. They are most suitable for the preparation of dry, wettable products of this invention and dispersants. Occasionally a liquid, non-ionic compound which is primarily an emulsifier, may serve as both wetter and dispersant.

Most preferred wetting agents are alkylbenzene and alkylnapthalene sulfonates, sulfated fatty alcohols, amines or acid amides, long chain esters of sodium isethionate, esters of sodium sulfosuccinate, sulfated or sulfonated vegtable oils, and ditertiary acetylenic glycols. Preferred dispersants are methyl cellulose, polyvinyl alcohol, lignin sulfonates, polymeric alkylnapthalene sulfonates, sodium napthalene sulfonates, polymethylene bisnaphthalene sulfonate and sodium-N-methyl-N-(long chain acid) taurates.

Wetting and dispersing agents in these preferred wettable powder compositions of the invention are usually present at concentrations of from about 0.5 weight percent to 5 weight percent. The inert extender then completes the formulation. Where needed, 0.1 weight percent of the extender may be replaced by a corrosion inhibitor or an anti-foaming agent or both.

Thus, wettable powder formulations of the invention will contain from about 25 to 90 weight percent active material, from 0.5 to 2.0 percent wetting agent, from 0.25 to 5.0 weight percent dispersant, and from 9.25 to 74.25 weight percent inert extender, as these terms are described above.

When the wettable powder contains a corrosion inhibitor or an anti-foaming agent or both, the corrosion inhibitor should not exceed about 1 percent of the composition, and the anti-foaming agent should not exceed about 0.5 percent by weight of the composition, both replacing equivalent amounts of the inert extender.

EXAMPLE 5

Dusts

Dusts are dense powder compositions which are intended for application in dry form. Dusts are characterized by their free-flowing and rapid settling properties so that they are not readily windborn to areas where their presence is not desired. They contain primarily an active ingredient and a dense, free-flowing, solid extender. Their performance is sometimes aided by the inclusion of a wetting agent, and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and anti-foam agents may also be used as components of a dust.

Thus, the dust compositions of this invention can comprise from about 0.5 to 20.0 weight percent active ingredient, 5 to 25 weight percent filler, 0 to 1.0 weight percent wetting agent and from about 30 to 90 weight percent dense, free-flowing extender, as these terms are used herein. Such dust formulations can contain, in addition, minor amounts of dispersants, corrosion inhibitors, and anti-foam agents derived from the wettable powders used to make the dust.

EXAMPLE 6

Emulsifiable Oils

Emulsifiable oils are usually solutions or suspensions of active material in non-water miscible solvents together with a surfactant and/or emulsifier.

For compositions of this invention, emulsifiable oil compositions can be made by mixing the active ingredient with an organic solvent and surfactant. Suitable solvents for the compositions of this invention are chlorinated solvents, water immiscible ethers, esters, or ketones alone or in admixture with aromatic hydrocarbons. Suitable surfactants are those ionic or non-ionic agents known to the art as emulsifying agents.

Emulsifying agents most suitable for the emulsifiable oil compositions of this invention are long chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates, or preferably mixtures of these emulsifying agents. Such emulsifying agents should comprise from about 1 to 10 weight percent of the total composition. As described above, however, up to 5 parts of emulsifying agent for each part of active ingredient can be used.

Thus, emulsifiable oil compositions of the present invention can consist of from about 10 to 50 weight percent active ingredient, about 40 to 82 percent solvents, and about 1 to 10 weight percent emulsifier, as these terms are defined and used above.

EXAMPLE 7

Granules

Granules are physically stable, particulate compositions containing spores and-or mycelium of this invention which adhere to or are distributed through a basic matrix of a coherent, inert carrier with microscopic dimensions. In order to aid leaching of the active ingredient from the granule, a surfactant can be present.

The inert carrier is preferably of mineral origin, and suitable carriers are natural clays, some pyrophyllites and vermiculite. Suitable wetting agents can be anionic or non-ionic.

For the granule compositions of this invention, most suitable carriers are of two types. The first are porous, absorptive pre-formed granules, such as preformed and screened granular attapulgite or heat expanded, granular, screened vermiculite. On either of these, a solution of the active agent can be sprayed and will be absorbed at concentrations up to 25 weight percent of the total weight. The second type are initially powdered kaolin clays, hydrated attapulgite or bentonite clays in the form of sodium, calcium or magnesium bentonites. Water-soluble salts such as sodium salts may also be present to aid in the disintegration of the granules in the presence of moisture. These ingredients are blended with the active components to give mixtures that are granulated, followed by drying to yield formulations with the active component distributed uniformly throughout the mass. Such granules can also be made with 25 to 30 weight percent active component but more frequently a concentration of about 10 weight percent is desired for optimum distribution. The granular compositions of this invention are believed to be most useful in a size range of 15–30 mesh.

The most suitable wetting agents for the granular compositions of this invention depend upon the type of granule used. When pre-formed granules are sprayed with active material in liquid form, the most suitable wetting agents are non-ionic, liquid wetters miscible with the solvent. These are more generally known in the art as emulsifiers and comprise alkylaryl polyether alcohols, alkyl polyether alcohols, polyoxyethylene sorbitan fatty acid esters, polyethylene glycol esters with fatty or rosin acids, fatty alkylol amide condensates, oil soluble petroleum or vegetable oil sulfonates, or mixtures of these. Such agents will usually comprise up to about 5 weight percent of the total composition.

When the active ingredient is first mixed with a powdered carrier and subsequently granulated, liquid non-ionic wetters can still be used, but it is usually preferable to incorporate at the mixiing stage, one of the solid, powdered anionic wetting agents such as those previously listed for the wettable powders. Such agents should comprise about 0 to 2 weight percent of the total composition.

Thus, the preferred granular formulations of this invention comprise about 5 to 30 weight percent active material, about 0 to 5 weight percent wetting agent, and about 65 to 95 percent inert mineral carrier, as these terms are used herein.

What we claim is:

1. A mycoherbicide concentrate for the preparation of compositions effective to control waterhyacinth, said concentrate comprising: the microorganism *Cercospora rodmanii* Conway adsorbed on an agronomically acceptable carrier.

2. A mycoherbicide concentrate for the preparation of compositions effective to control waterhyacinth said concentrate comprising a slurry of the microorganism *Cercospora rodmanii* Conway.

3. A mycoherbicide composition for the control of waterhyacinth said composition comprising: the microorganism *Cercospora rodmanii* Conway and an agronomically acceptable carrier.

4. The mycoherbicide of claim 3 in combination with an insect or fungi effective in the control of waterhyacinth.

5. A wettable powder composition useful in the conrol of waterhyacinth said composition comprising:

25–90% of the microorganism *C. rodmanii* Conway,
0.5–2% of a wetting agent,
0.25–5% of a dispersant, and
9–75% inert extender 6. A dust composition useful in the control of waterhyacinth said composition comprising:

0.5–20% of the microorganism *C. rodmanii* Conway,
5–25% of a dense filler,
0–1% of a wetting agent, and
30–90% of an extender.

7. An emulsifiable oil composition useful in the control of waterhyacinth said composition comprising:

10–50% of the microorganism *C. rodmanii* Conway,
40–82% of a suitable solvent, and
1–10% of an emulsifier.

8. A granule composition useful in the control of waterhyacinth said composition comprising:

5–30% of the microorganism *C. rodmanii* Conway,
0–5% of a wetting agent, and
65–95% of an inert carrier.

9. A method for controlling the growth of waterhyacinth said method comprising treating the waterhyacinth with a microorganism comprising *Cercospora rodmanii* Conway.

10. The method of claim 9 wherein the microorganism is applied to the waterhyacinth in an amount of from 0.1–100 kg per hectare of area to be treated.

* * * * *

UNITED STATES PATENT AND TRADEMARK OFFICE

CERTIFICATE OF CORRECTION

PATENT NO. : 4,097,261

DATED : June 27, 1978

INVENTOR(S) : Kenneth Edward Conway, et al.

It is certified that error appears in the above—identified patent and that said Letters Patent is hereby corrected as shown below:

Title page, column 1, "Assignee. Abbott Laboratories, North Chicago, Ill." should read -- Assignee: University of Florida, Gainesville, FL. --.

Signed and Sealed this

*Fourth* Day of *August 1981*

[SEAL]

*Attest:*

GERALD J. MOSSINGHOFF

*Attesting Officer* *Commissioner of Patents and Trademarks*